United States Patent [19]

Caines

[11] 4,392,380
[45] Jul. 12, 1983

[54] HIGH TEMPERATURE PRESSURE COUPLED ULTRASONIC WAVEGUIDE

[75] Inventor: Michael J. Caines, Forest Park, Ill.

[73] Assignee: The United States of America as represented by the United States Department of Energy, Washington, D.C.

[21] Appl. No.: 233,354

[22] Filed: Feb. 11, 1981

[51] Int. Cl.$^3$ .............................. G01N 29/00
[52] U.S. Cl. ............................ 73/644; 73/599; 73/632
[58] Field of Search ............... 73/632, 644, 597, 599, 73/622

[56] References Cited

U.S. PATENT DOCUMENTS

| 2,458,581 | 1/1949 | Firestone et al. | 73/644 |
| 3,182,490 | 5/1965 | Gibson | 73/644 |
| 3,987,674 | 10/1976 | Baumoel | 73/597 |
| 4,014,211 | 3/1977 | Araki et al. | 73/632 |
| 4,019,373 | 4/1977 | Freeman et al. | 73/644 |
| 4,242,744 | 12/1980 | Rottman | 73/644 |

*Primary Examiner*—Howard A. Birmiel

[57] ABSTRACT

A pressure coupled ultrasonic waveguide is provided to which one end may be attached a transducer and at the other end a high temperature material for continuous ultrasonic testing of the material. The ultrasonic signal is coupled from the waveguide into the material through a thin, dry copper foil.

7 Claims, 2 Drawing Figures

U.S. Patent  Jul. 12, 1983  4,392,380
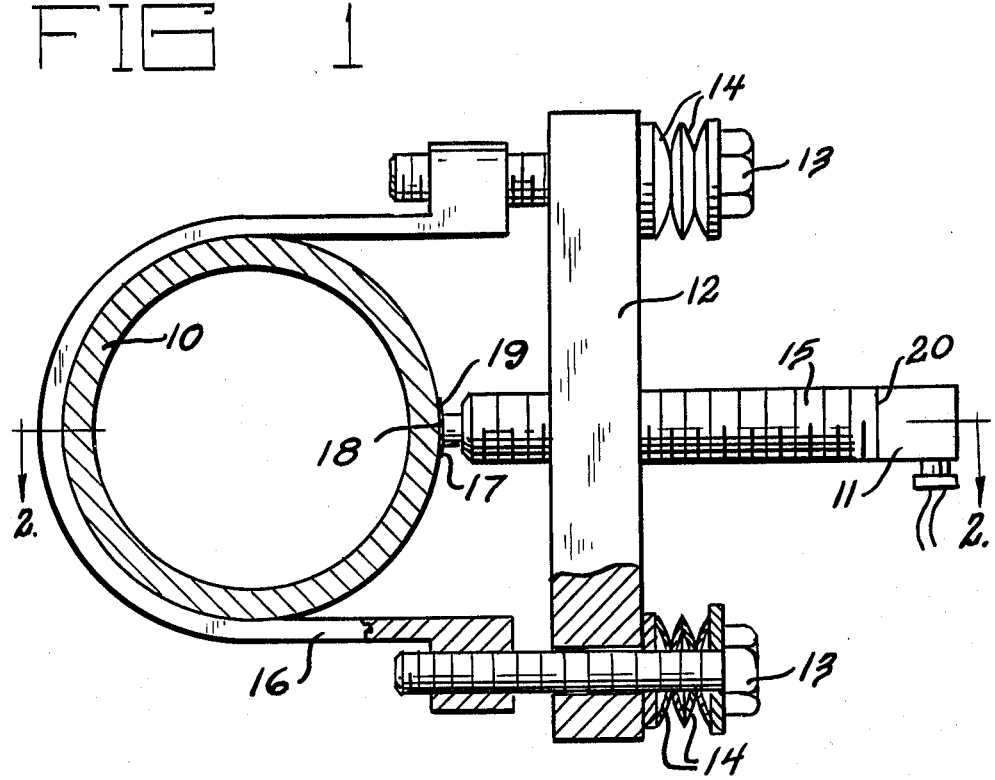
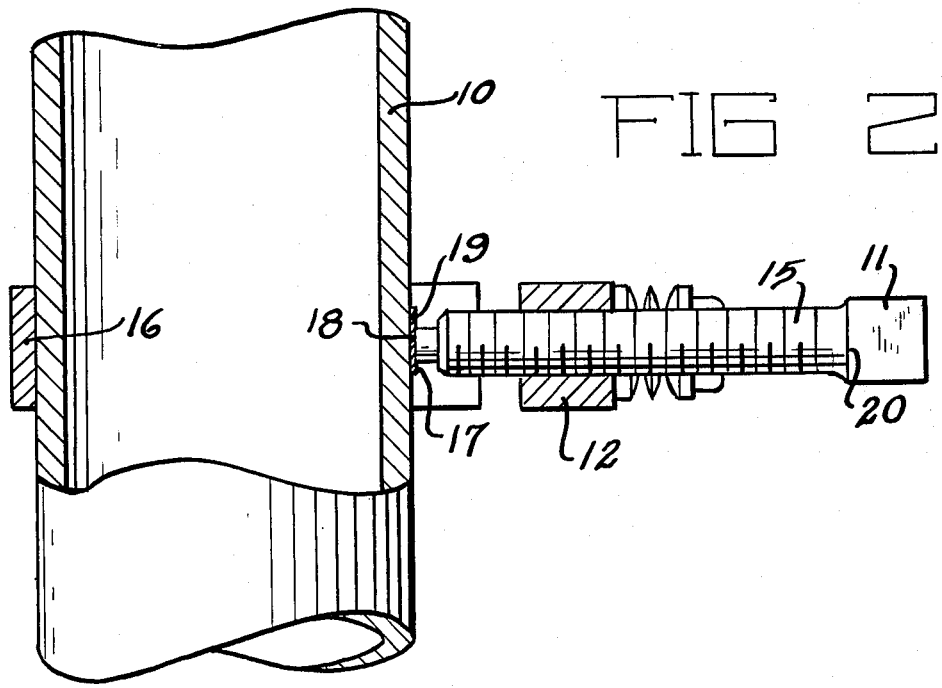

4,392,380

HIGH TEMPERATURE PRESSURE COUPLED ULTRASONIC WAVEGUIDE

CONTRACTUAL ORIGIN OF THE INVENTION

The United States Government has rights in this invention pursuant to Contract No. W-31-109-ENG-38 between the U.S. Department of Energy and Argonne National Laboratory.

BACKGROUND OF THE INVENTION

The present invention relates to ultrasonic nondestructive monitoring of a high temperature material. The commercially available ultrasonic transducers used to introduce the ultrasonic signal into the test specimen cannot continuously withstand the high operating temperatures encountered in high temperature operation.

The prior art technique for allowing high-temperature ultrasonic testing of materials utilizes a waveguide positioned between the test specimen and the transducer. The waveguide transmits the ultrasonic signal from the transducer to the specimen and the reflected echo from the specimen back to the transducer while at the same time providing a path between the hot specimen and the transducer over which temperature decays from the hot specimen to the transducer. One example of such prior art devices is U.S. Pat. No. 3,350,923, Nov. 17, 1967, of Cross, which uses a waveguide welded to pipes in order to ultrasonically measure wall thickness at elevated temperature. Welding metallurgically alters the wall of the test specimen. This change causes noisy signal and destroys the continuity of the pipe. Cross describes a variety of weld joints between the waveguide and the test specimen wall, all designed to achieve a reflective surface at the interface which would generate an interface echo signal approximately equal in amplitude to the back wall echo signal. Cross specifies that no more than 50% of the cross-sectional area of the delay line should be fused to the pipe in order to achieve an interface echo signal amplitude equal to the back wall echo signal amplitude. Threading of the outer surface of the waveguide is used by Cross to reduce signal side wall reflections.

It is therefore an object of this invention to provide an improved device for coupling a waveguide to a test specimen.

Another object of this invention is to provide a pressure coupling for an ultrasonic waveguide to a material in high-temperature applications to avoid metallurgical altering of material.

Another object of the invention is to provide a waveguide that is temporarily connected to the test material without deforming the test material.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF INVENTION

An ultrasonic device is provided for monitoring the characteristics of a material. The device consists of an ultrasonic waveguide and an adjustable holding fixture. The waveguide is a threaded rod that is coupled on one end to the test material by a foil; on the other end of the waveguide an ultrasonic transducer is mounted thereon. The holding fixture consists of a saddle enclosing the material and a crossbar connected by bolts with spring washers between the bolts and crossbar. The waveguide is threaded in the crossbar.

BRIEF DESCRIPTION OF DRAWINGS

FIG. 1 is a section of the improved ultrasonic waveguide herein disclosed; and

FIG. 2 is a section through line 2—2 of FIG. 1.

DETAILED DESCRIPTION OF THE INVENTION

Referring to FIG. 1, there is shown an improved device for ultrasonically testing a material. Material 10, from which certain information such as material thickness is to be obtained ultrasonically, may, for example, be a pipe. Any type of material could be tested by this system by changing dimensions and configuration of the saddle. A transducer 11 is used to transmit and receive the ultrasonic signal sent to and received from the material 10. State-of-the-art ultrasonic transducers cannot withstand high operating temperatures. To protect transducer 11, a waveguide 15 is provided which is pressure coupled at curved end 18 to the wall 19 of material 10 with a copper foil 17 positioned betwen end 18 and wall 19. At the other end 20 of the waveguide 15 is mounted transducer 11.

The waveguide 15 is intended to decay the temperature from the hot wall 18 of the material 10 to an acceptable level at transducer 11 while at the same time providing a path for ultrasonic wave to travel between transducer 11 and material 10.

The waveguide 15 is a threaded rod; it is threaded to reduce signal sidewall reflections and to connect with crossbar 12. The waveguide 15 is mechanically attached to the material 10 without welding which would metallurgically alter the material of wall 19. The pressure coupling does not deform the material wall 19. The waveguide holding fixture for obtaining the pressure coupling consists of a saddle 16 enclosing the material 10 and connected slip fit with bolts 13 to a cross bar 12. A center threaded hole of crossbar 12 receives the threaded waveguide 15. Spring washers 14 are used between the cross bar 12 and bolts 13 to keep a constant load on the waveguide 15. The preferred material of this holding fixture and waveguide 15 is type 304 stainless steel because of its resistance to creep or slow change in dimensions of the saddle 16 at temperatures and stresses for which this system is designed, temperatures up to 700° C. ($\sim$ 1300° F.) and stress up to $13 \times 10^6$ pa (2000 psi).

The spring washers 14 are located on a portion of the saddle 16 fat enough away from the material wall so that they are not exposed to high temperatures which would cause relaxation. One condition for good transmission of the ultrasonic signal through the interface between the material wall 19 and the waveguide outer surface 18 through the copper foil 17 is that the surface be smooth. In *Ultrasonic Testing of Materials*, Second Edition, Springer-Verlag, New York (1977) by Josef Krautkramer and Herbert Krautkramer at page 20 states that a roughness of more than approximately one-tenth of the wavelength difference of the ultrasound in height markedly impairs the coupling; the acoustic pressure in the axial direction is reduced and greater scattering occurs. This scattering causes a loss in the total acoustic pressure available to penetrate the material wall 19.

The preferred frequency of the ultrasonic transducer used in this system is 7.5 MHz; having a wavelength of 0.77 mm. The material wall 19 and the waveguide 18 are polished to the same finish. The polishing process uses several grades of abrasives, graduating to a one micron (1-$\mu$) diamond paste providing a polished surface of fifty hundredths micrometers (0.50 $\mu$m). The couplant 17 between the material wall 19 and the waveguide outer surface 18 needed is one which does not deteriorate at high pressures and high temperature. Various types of liquids and pastes were evaluated, but none performed for extended periods above 500° C. Several metal foils defined to be between 0.001–0.050 inch, including gold, platinum, aluminum, and copper were evaluated and all of these transmit ultrasonic energy but copper is preferred. Using a foil that is too thin did not give good mechanical coupling being too thin to fill in voids. Foil that is too thick attenuates the ultrasonic signal in the foil. It was determined experimentally that annealed copper with a nominal thickness of 0.010 inch or 0.030 inch gave the preferred ultrasonic coupling with the least amount of coupling pressure, owing to its low coefficient of reflection of ultrasonic energy.

The copper foil 17 is first annealed to soften it and cleaned to remove surface oxidation before it is placed between the waveguide 18 and the material wall 19. After the copper foil 17 is in place it is compressed by the force of the waveguide pushing it against the material wall 19. Transmission can be improved by again annealing the foil in place with a torch or electric heater. The pressure needed was experimentally discovered for useable signals is 50 to 70$\times$10$^6$ Pascals (approximately 7,000 to 10,000 psi).

I claim:

1. A device for ultrasonically monitoring the characteristics of a material comprising:
   a threaded waveguide;
   a transducer coupled to one end of the waveguide;
   a treated copper foil positioned between the material and the other end of the waveguide, wherein the treatment of said treated foil comprises annealing and polishing to render the foil soft and smooth;
   an adjustable holding fixture for positioning the waveguide against the foil and against the material; and
   force compensating means for maintaining substantially constant pressure against the waveguide and against the material during creep of said fixture wherein said force compensating means is positioned far enough away from the material so as not to be exposed to temperatures of such a high level as to cause relaxation of said force compensating means.

2. The device of claim 1 wherein the copper foil is thick enough for mechanical coupling to fill in voids without attenuating an ultrasonic signal.

3. The device of claim 1 wherein the copper foil is annealed after being positioned between the material and the waveguide.

4. The device of claim 1 wherein the threaded waveguide is made of 304 stainless steel.

5. The device of claim 1 wherein the adjustable holding fixture comprises:
   bolts;
   a saddle enclosing the material and having two threaded holes for receiving the bolts;
   a crossbar having two outer holes for receiving the bolts and a threaded center hole for receiving the threaded waveguide, the crossbar being coupled to the saddle by the bolts passing through the outer holes;
   and wherein the force compensating means comprise spring washers positioned between the head ends of the bolts and the crossbar;
   whereby tightening of the bolts exerts pressure forcing the waveguide against the material.

6. A device for ultrasonically monitoring the characteristics of a material comprising:
   a threaded waveguide;
   a transducer coupled to one end of the waveguide;
   a treated copper foil positioned between the material and the other end of the waveguide, wherein the treatment of said treated foil comprises annealing and polishing to render the foil soft and smooth;
   adjustable constant pressure means for poisitioning the foil between the material and the waveguide whereby an adjustable constant pressure is applied to the waveguide against the foil and against the material wherein the adjustable constant pressure means comprises: bolts;
   a saddle enclosing the material and having two threaded holes for receiving the bolts;
   spring washers; and
   a crossbar having two outer holes for receiving the bolts and a threaded center hole for receiving the threaded waveguide, the crossbar being coupled to the saddle by the bolts passing through the outer holes with the spring washers being positioned beetween the head end of the bolts and the crossbar, with tightening of the bolts, hereby exerting pressure forcing the waveguide against the material.

7. The device of claim 6 wherein the threaded waveguide and the adjustable constant pressure means are made of 304 stainless steel.

* * * * *